(12) United States Patent
Wenchell

(10) Patent No.: US 9,364,231 B2
(45) Date of Patent: Jun. 14, 2016

(54) SYSTEM AND METHOD OF USING SIMULATION RELOAD TO OPTIMIZE STAPLE FORMATION

(71) Applicant: Covidien LP, Mansfield, MA (US)

(72) Inventor: Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 685 days.

(21) Appl. No.: 13/633,213

(22) Filed: Oct. 2, 2012

(65) Prior Publication Data

US 2013/0110088 A1    May 2, 2013

Related U.S. Application Data

(60) Provisional application No. 61/551,956, filed on Oct. 27, 2011.

(51) Int. Cl.

| | | |
|---|---|---|
| A61B 17/068 | (2006.01) | |
| A61B 19/00 | (2006.01) | |
| A61B 17/072 | (2006.01) | |
| A61B 17/00 | (2006.01) | |
| A61B 17/29 | (2006.01) | |
| A61B 17/32 | (2006.01) | |

(52) U.S. Cl.
CPC ......... *A61B 17/07207* (2013.01); *A61B 17/068* (2013.01); *A61B 19/46* (2013.01); *A61B 2017/00017* (2013.01); *A61B 2017/00022* (2013.01); *A61B 2017/00398* (2013.01); *A61B 2017/00464* (2013.01); *A61B 2017/00473* (2013.01); *A61B 2017/00725* (2013.01); *A61B 2017/00734* (2013.01); *A61B 2017/2927* (2013.01); *A61B 2017/320052* (2013.01); *A61B 2019/465* (2013.01)

(58) Field of Classification Search
CPC ............... A61B 17/07207; A61B 2017/00464; A61B 2017/00017; A61B 2019/464
See application file for complete search history.

(56) References Cited

U.S. PATENT DOCUMENTS

| | | |
|---|---|---|
| 3,866,510 A | 2/1975 | Eibes et al. |
| 5,518,164 A | 5/1996 | Hooven |

(Continued)

FOREIGN PATENT DOCUMENTS

| | | |
|---|---|---|
| EP | 0 834 280 A1 | 4/1998 |
| EP | 1 273 272 A2 | 1/2003 |
| JP | 9 149 906 A | 6/1997 |

OTHER PUBLICATIONS

European Search Report corresponding to European Application No. 10 01 2659.8, completed Dec. 21, 2010; mailed Jan. 3, 2011; 3 pages.

(Continued)

*Primary Examiner* — Andrew M Tecco

(57) ABSTRACT

The present disclosure is directed to a testing systems and methods for testing a powered surgical instrument. The powered surgical instrument includes a processor configured to control operation of the powered surgical instrument, a memory configured to store a tissue compression program, a reload configured to clamp tissue, a motor configured to control the reload to apply a compressive force to the tissue by the reload, and at least one sensor configured to measure a current draw on the motor. The processor executes the simulation program to measure the current draw on the motor through a nominal thickness firing and the measured current draw is used to adjust the tissue compression program.

4 Claims, 5 Drawing Sheets

(56) References Cited

U.S. PATENT DOCUMENTS

| | | | |
|---|---|---|---|
| 5,886,246 | A | 3/1999 | Bareggi et al. |
| 7,922,063 | B2* | 4/2011 | Zemlok et al. ............. 227/176.1 |
| 8,062,236 | B2* | 11/2011 | Soltz ............................. 600/587 |
| 8,551,025 | B2* | 10/2013 | Soltz ............................. 600/587 |
| 8,900,164 | B2* | 12/2014 | Soltz ............................. 600/587 |
| 8,968,217 | B2* | 3/2015 | Soltz ............................. 600/587 |
| 2001/0007074 | A1 | 7/2001 | Strobel et al. |
| 2003/0009441 | A1 | 1/2003 | Holsten et al. |
| 2003/0105478 | A1* | 6/2003 | Whitman et al. ............. 606/167 |
| 2003/0125717 | A1* | 7/2003 | Whitman ......................... 606/1 |
| 2004/0094597 | A1* | 5/2004 | Whitman et al. ........... 227/180.1 |
| 2004/0111081 | A1* | 6/2004 | Whitman et al. ................. 606/1 |
| 2007/0179408 | A1* | 8/2007 | Soltz ............................. 600/587 |
| 2008/0255413 | A1* | 10/2008 | Zemlok et al. ................ 600/106 |
| 2009/0012556 | A1 | 1/2009 | Boudreaux et al. |
| 2009/0057369 | A1 | 3/2009 | Smith et al. |
| 2009/0108048 | A1* | 4/2009 | Zemlok et al. ............. 227/175.1 |
| 2010/0270355 | A1* | 10/2010 | Whitman et al. .......... 227/176.1 |
| 2011/0011915 | A1 | 1/2011 | Shelton, IV |
| 2011/0024479 | A1 | 2/2011 | Swensgard et al. |
| 2011/0121049 | A1* | 5/2011 | Malinouskas et al. ..... 227/175.1 |
| 2011/0125138 | A1* | 5/2011 | Malinouskas et al. ............ 606/1 |

OTHER PUBLICATIONS

European Search Report corresponding to European Application No. 10 01 2646.5, completed Feb. 11, 2011; mailed Feb. 22, 2011; 3 pages.

European Search Report corresponding to European Application No. 12 19 0101, dated Feb. 12, 2015; 9 pages.

Chinese Office Action dated Dec. 17, 2015, issued in Chinese Application No. 201210418425.

Australian Examination Report 1 dated Aug. 28, 2013, issued in Australian Application No. 2012238268.

Australian Examination Report 2 dated Oct. 8, 2014, issued in Australian Application No. 2012238268.

* cited by examiner

SYSTEM AND METHOD OF USING SIMULATION RELOAD TO OPTIMIZE STAPLE FORMATION

CROSS REFERENCE TO RELATED APPLICATION

The present application claims the benefit of and priority to U.S. Provisional Application Ser. No. 61/551,956, filed on Oct. 27, 2011, the entire contents of which are incorporated herein by reference.

BACKGROUND

1. Technical Field

The present disclosure relates generally to medical devices. More specifically, the present disclosure relates generally to systems and methods for controlled tissue compression.

2. Background of the Related Art

Some surgical procedures require the compression, e.g., clamping, of a patient's tissue. Such procedures may include, e.g., anastomosing, stapling, and resecting of tissue. For example, where cancerous tissue is identified in a patient's gastrointestinal tract, the cancerous tissue may need to be surgically removed. Where, for example, the cancerous tissue is located on the colon and is accessible by surgical instrumentation, the surgeon may make an incision in the patient's abdomen to allow access to the bowel. The surgeon may then use a linear cutting and stapling device, such as that described in U.S. patent application Ser. No. 12/235,362, filed on Sep. 22, 2008, which is expressly incorporated herein in its entirety by reference, to cut and staple the colon tissue on opposite sides of the cancerous portion to be removed. In this procedure, the colon is externally clamped (e.g., between opposed jaws) to compress the tissue. While the tissue is compressed, a cutter and a stapler are activated to make a linear cut and apply typically two linear rows of staples in the areas adjacent the cut. The stapling thus closes both open ends of the portion of the bowel to be removed, as well as providing a temporary closure of the two cut ends of the bowel. This closure limits exposure of the surrounding tissue to the interior of the bowel, thus limiting the risk of infection. After the cutting and stapling procedure, the cancerous portion of tissue may be removed from the patient's body.

After the resection of the cancerous tissue, the surgeon may employ an anastomosing and stapling device, e.g., a circular stapler/cutter. During this procedure, a head portion is positioned within the colon adjacent one of the cut ends and a base or shaft portion is positioned within the colon adjacent the other cut end. The head portion and the base portion may be coupled via a shaft and/or cable that extends out of one cut end and into the other. Via this coupling, the surgeon is able to actuate the anastomosing and stapling device to draw the head portion and the base portion together. After the two cut ends of the colon contact each other, the actuation continues such that the two portions of the colon are clamped together at an annular area of contact. While clamped, the anastomosing and stapling device may be further actuated to apply an annular ring of staples into the compressed tissue. The device may also cut excess tissue disposed within the colon. The head portion and the base portion are then moved apart and the anastomosing and stapling device removed from the patient.

To achieve effective stapling in the above procedures, the tissue must be compressed to the extent that there is an adequately small tissue gap, e.g., one millimeter, between the faces of the tool. If the clamping structures of the instrument are exposed to enough force, maintaining a uniform target tissue gap across the length of tissue to be stapled may be difficult or even impossible. For example, where the clamping structures are cantilevered jaws of a linear stapler, the distal portion of the jaws may splay outwardly from each other under high clamping forces. Where one or both of the jaws splay in this manner, the tissue gap typically increases toward the distal ends of the jaws. Where this tissue gap exceeds an acceptable range, staples may not adequately close the tissue to prevent contamination. This may result from, e.g., the initial stapled gap being too large and/or failure of the staple (e.g., separation from one or more of the portions of stapled tissue) due to improper formation resulting from, e.g., too large a gap between a staple pusher and an anvil that closes the staple.

Powered stapling devices may use control systems and algorithms to control a driving motor in order to properly clamp tissue and achieve a desired tissue gap. Many of these algorithms use standard variables that are based on type of tissue being clamped, type of disease affecting the tissue, the stage of the disease, etc along with typical characteristics of the stapling device itself. However, because each stapling device is different due to motor variation, device construction, wear, mechanical tolerances and mechanical play etc., the variables used in one stapling device to achieve a desired tissue gap may not be effective in a different stapling device of the same type. There is a need to calibrate powered stapling devices and provide inputs to the device control systems in order to improve optimum tissue gaps and staple formation while stapling

SUMMARY

In an embodiment of the present disclosure a system and method for testing a powered surgical instrument is provided. The powered surgical instrument includes a processor configured to control operation of the powered surgical instrument, a memory configured to store a tissue compression program, a reload configured to clamp tissue, a motor configured to control the reload to apply a compressive force to the tissue by the reload, and at least one sensor configured to measure a current draw on the motor. The processor executes a simulation program to measure the current draw on the motor through a nominal thickness firing and the measured current draw is used to adjust the tissue compression program.

The tissue compression program includes programming code coefficients and the processor adjusts the programming code coefficients based on the measured current draw. The processor may compare the measured current draw to a predetermined current draw associated with the nominal thickness firing. The difference between the measured current draw and the predetermined current draw is used to adjust the programming code coefficients.

In another embodiment of the present disclosure, a simulation reload is provided that is configured to be coupled to a powered surgical instrument. The simulation reload may be factory calibrated and have known mechanical parameters of greater accuracy than actual reloads. The simulation reload may include a memory configured to store calibration parameters of the reload. The simulation reload may also include a memory configured to store a simulation program, a processor configured to execute the simulation program, and at least one sensor configured to measure a current draw on the motor of the powered surgical instrument. The processor executes the simulation program to measure the current draw on the motor through a nominal thickness firing and the measured current draw is stored in the memory. While the simulation program, processor and sensor are described as resident in the simulation In yet another embodiment of the present disclosure, a simulation system is provided. The simulation system includes a powered surgical instrument, a simulation reload, and a test platform. The powered surgical instrument includes a processor configured to control operation of the powered surgical instrument, a memory configured to store a tissue compression program, and a motor configured to control a reload to apply a compressive force to the tissue by the reload. The simulation system includes a memory configured to store a simulation program, a processor configured to execute the simulation program, and at least one sensor configured to measure a current draw on the motor of the powered surgical instrument. The simulation reload processor executes the simulation program to measure the current draw on the motor through a nominal thickness firing and the measured current draw is stored in the memory of the simulation reload. The test platform includes a first interface configured to be operatively connected to the powered surgical instrument and a second interface configured to be operatively connected to the simulation reload. The test platform is configured to adjust the tissue compression program stored in the memory of the powered surgical instrument based on the measured current draw stored in the memory of the simulation reload. While the simulation program, processor and sensor are described as resident in the simulation reload in one embodiment, these components may be located in any portion of the system provided with the provision of suitable data transmission between the components.

The tissue compression program includes programming code coefficients and the test platform adjusts the programming code coefficients based on the measured current draw. The test platform may compare the measured current draw to a predetermined current draw associated with the nominal thickness firing. The difference between the measured current draw and the predetermined current draw is used to adjust the programming code coefficients.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
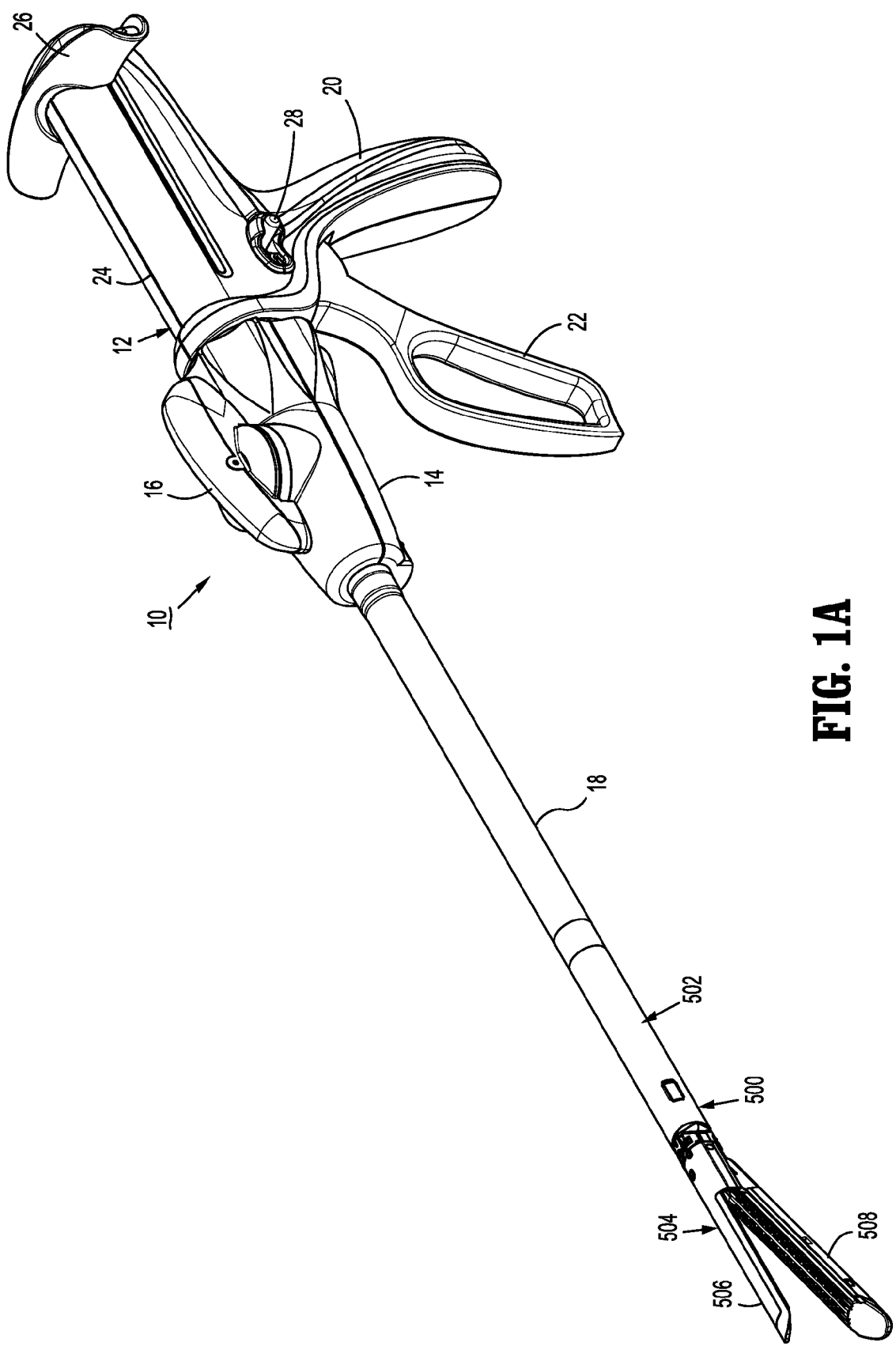
FIGS. 1A-1C are perspective views of powered surgical instruments according to embodiments of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (i.e., doctor, surgeon, nurse, or the like) performing a medical procedure involving the use of embodiments described herein.

As seen in FIG. 1A, powered surgical instrument, e.g., a surgical stapler, in accordance with the present disclosure is referred to as reference numeral 10. Powered surgical instrument 10 is merely an example of a surgical instrument that utilizes the embodiments of the present disclosure described herein. With reference to FIG. 1A, powered surgical instrument 10 includes a handle assembly 12, a rotation knob 14, an articulation lever 16, an elongated body portion 18 and a reload 500. Handle assembly 12 includes a stationary handle portion 20, a movable handle portion or trigger 22, a barrel portion 24, and retraction knobs 26. An actuator button 28 extends transversely through and projects outwardly from opposite sides of handle assembly 12.

Reload 500 includes a proximal body portion 502 and a tool assembly 504. Proximal body portion 502 is releasably attached to a distal end of elongated body portion 18 and tool assembly 504 is pivotably attached to a distal end of proximal body portion 502. Tool assembly 504 includes an anvil assembly 506 and a cartridge assembly 508. Cartridge assembly 508 is pivotal in relation to anvil assembly 506 from an open or unclamped position to a closed or clamped position.

Figure 1B:
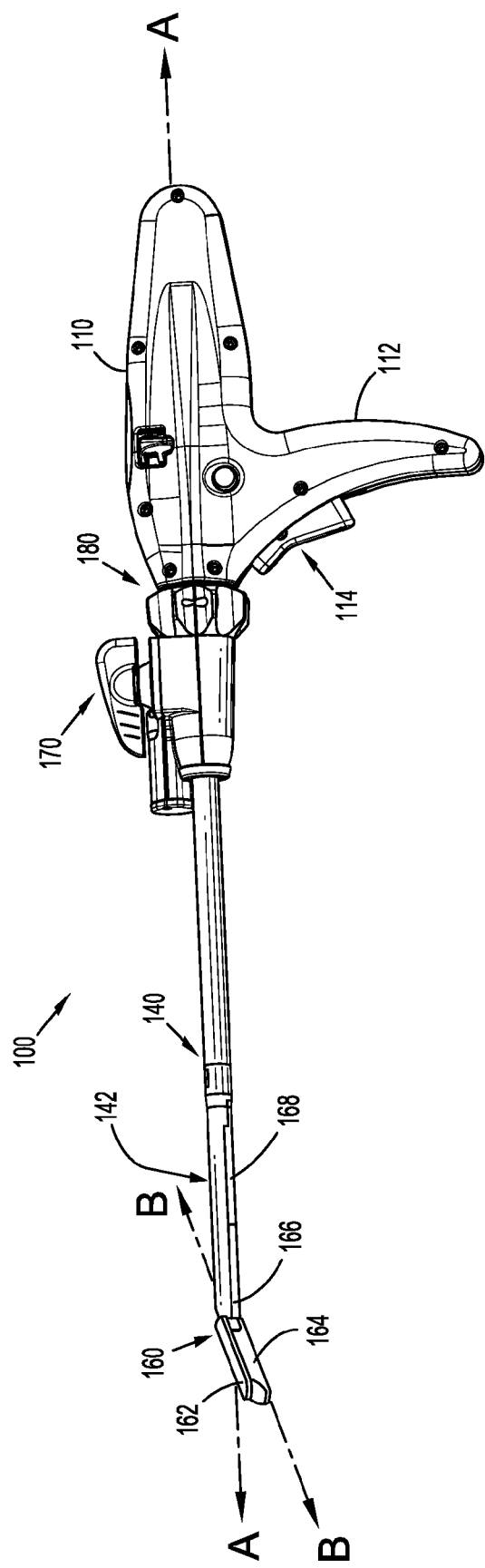

As seen in FIG. 1B, another powered surgical instrument, e.g., a surgical stapler, in accordance with the present disclosure is referred to in the figures as reference numeral 100. With reference to FIG. 1B, powered surgical instrument 100 includes a housing 110, an endoscopic portion 140 defining a first longitudinal axis A-A extending therethrough, and an end effector 160, defining a second longitudinal axis B-B extending therethrough. Endoscopic portion 140 extends distally from housing 110 and end effector 160 is disposed adjacent a distal portion 142 of endoscopic portion 140. Housing 110 includes a handle portion 112 having at least one switch 114 thereon.

Powered surgical instrument 100 also includes an articulation mechanism 170. Actuation of articulation mechanism 170 causes end effector 160 to move from its first position, where longitudinal axis B-B is substantially aligned with longitudinal axis A-A, towards a position in which longitudinal axis B-B is disposed at an angle to longitudinal axis A-A. A plurality of articulated positions is achieved. Articulation mechanism 170 is mounted to a rotating housing assembly 180.

End effector 160 includes a cartridge assembly (e.g., jaw member 164) and an anvil assembly (e.g., jaw member 162) including an anvil portion for forming the surgical fasteners when deployed from the cartridge assembly. Cartridge assembly 164 has a cartridge body that houses a plurality of staples. At least one of anvil assembly 162 and cartridge assembly 164 is movable in relation to one another between an open position where anvil assembly 162 is spaced from cartridge assembly 164 and an approximated position for clamping tissue where anvil assembly 162 is in juxtaposed alignment with cartridge assembly 164. In an embodiment, the staples housed in cartridge assembly 164 are arranged to apply linear rows of staples to body tissue.

It is further envisioned that end effector 160 is attached to a mounting portion 166, which is pivotably attached to a body portion 168. Body portion 168 may be integral with endoscopic portion 140 of powered surgical instrument 100, or may be removably attached thereto to provide a replaceable, disposable loading unit (DLU) or single use loading unit (SULU). The loading unit may be connectable to endoscopic portion 140 through a bayonet connection or other suitable quick connect features. It is envisioned that the loading unit has an articulation link connected to mounting portion 166 of the loading unit and the articulation link is connected to a linkage rod so that the end effector 160 is articulated as the linkage rod is translated in the distal-proximal direction along first longitudinal axis A-A. Other means of connecting end effector 160 to endoscopic portion 140 to allow articulation may be used. For example, a flexible tube or a plurality of pivotable members may be used. Alternatively, the cartridge assembly or a portion thereof may be replaceable or removable.

A loading unit may incorporate (or be configured to incorporate) various end effectors, such as vessel sealing devices, linear stapling devices, circular stapling devices, cutters, etc. Such end effectors may be coupled to endoscopic portion 140 of powered surgical instrument 100. An intermediate flexible shaft may be included between handle portion 112 and loading unit. An example of a flexible shaft is described in detail in commonly-owned U.S. patent application Ser. No. 11/786,934, entitled "Powered Surgical Instrument", filed on Apr. 13, 2007, the contents of which are hereby incorporated by reference in their entirety.

Further details of powered surgical instrument 100 are described in detail in commonly-owned U.S. patent application Ser. No. 11/724,733 entitled "Surgical Stapling Apparatus with Powered Articulation", filed on Mar. 15, 2007, now U.S. Pat. No. 7,431,188, the contents of which are hereby incorporated by reference in their entirety.

Figure 1C:
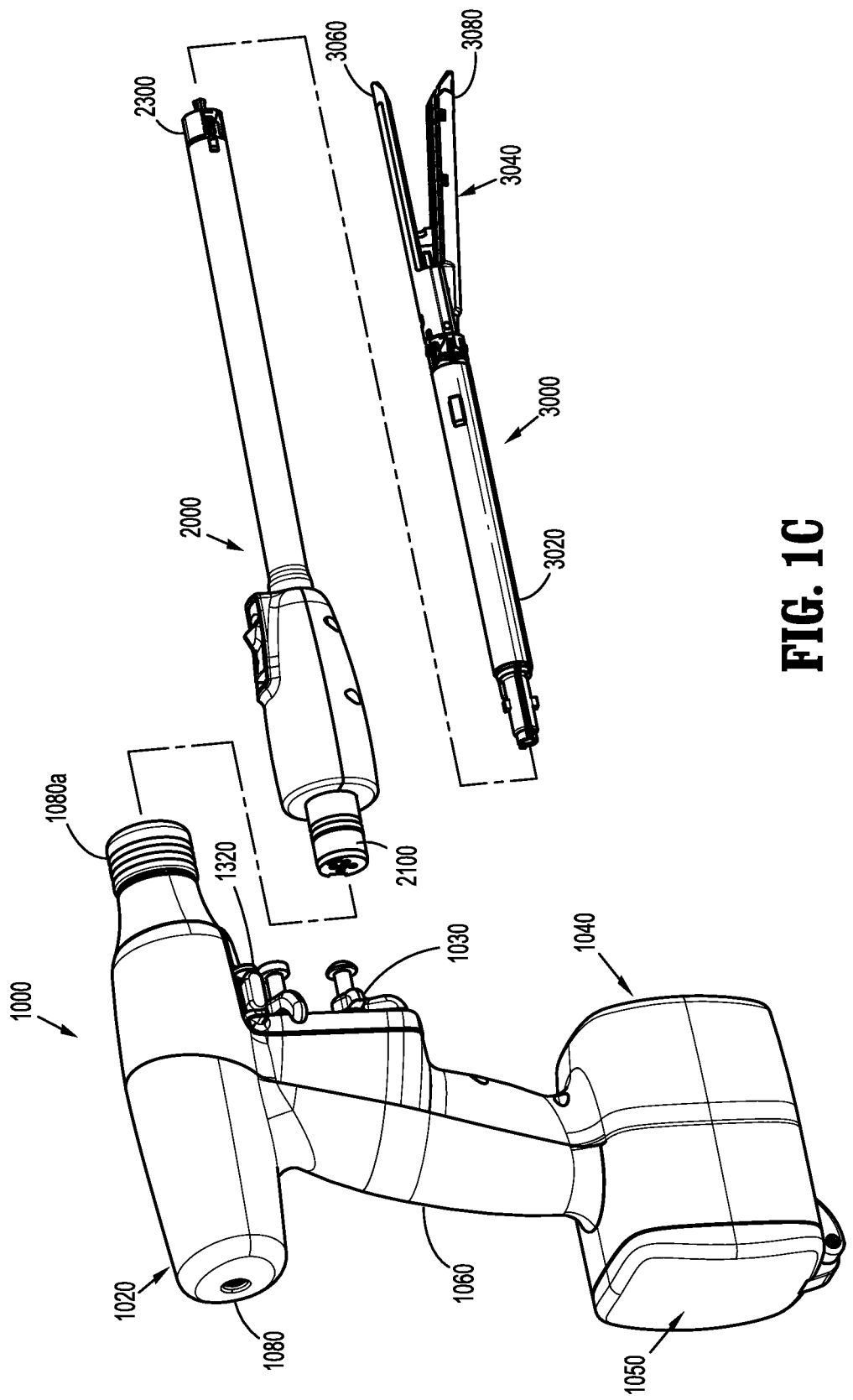

As seen in FIG. 1C, another powered surgical instrument, e.g., a surgical stapler, in accordance with the present disclosure is referred to in the figures as reference numeral 1000. With reference to FIG. 1B, powered surgical instrument 1000 includes a handle housing 1020 having a lower housing portion 1040, an intermediate housing portion 106 extending from and/or supported on lower housing portion 1004, and an upper housing portion 1080 extending from and/or supported on intermediate housing portion 1060.

Upper housing portion 1080 defines a connecting portion 1080a configured to accept a corresponding drive coupling assembly 2100 of adapter 2000.

As seen in FIG. 1C, powered surgical instrument 1000 includes a fire button or safety switch 1320 supported between intermediate housing portion 1060 and upper housing portion 1080, and situated above trigger housing 1030. In use, tool assembly 3040 is actuated between opened and closed conditions as needed and/or desired. Powered surgical instrument 1000 is configured to move anvil assembly 3060 relative to cartridge assembly 3080 of reload 3000, and/or to fire a stapling and cutting cartridge within cartridge assembly 3080 of reload 3000.

In order to fire reload 3000, to expel fasteners therefrom when tool assembly 3040 of reload 3000 is in a closed condition, safety switch 1320 is depressed thereby instructing powered surgical instrument 1000 that reload 3000 is ready to expel fasteners therefrom.

Figure 2:
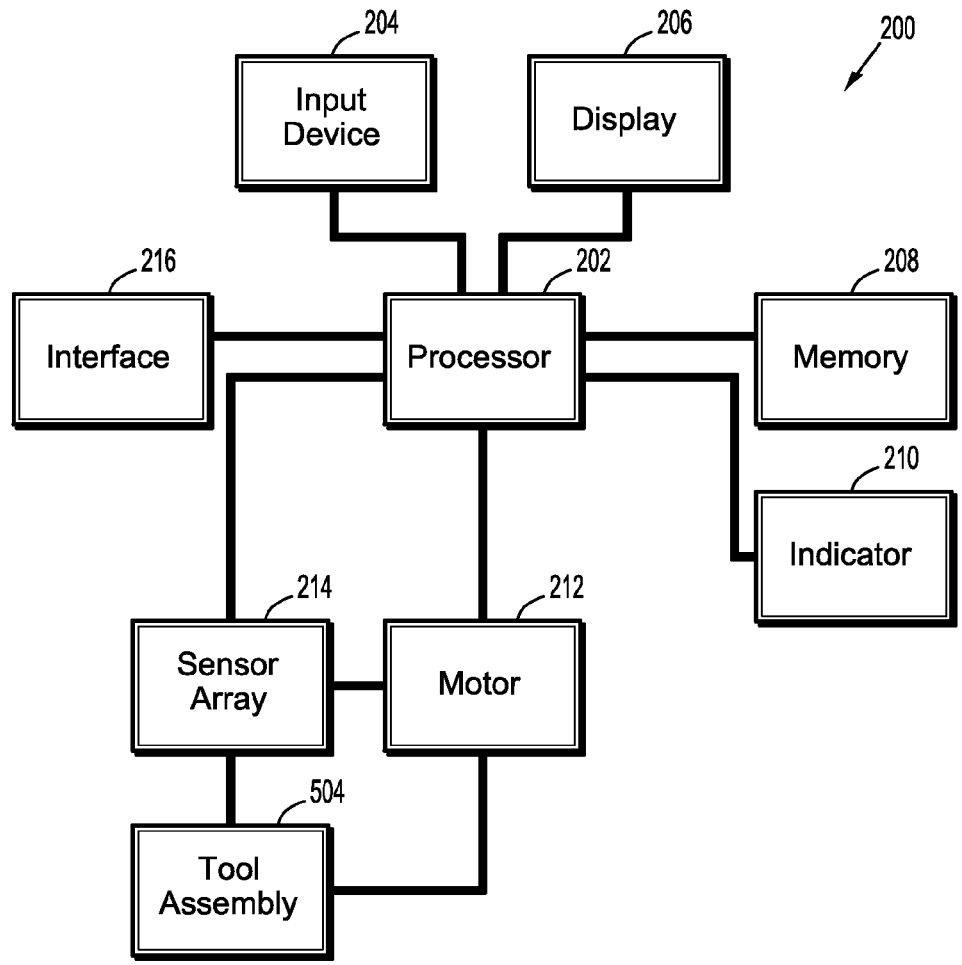
FIG. 2 is a system block diagram of a powered surgical instrument according to an embodiment of the present disclosure.

As seen in FIG. 2, powered surgical instrument 10, 100, and 1000 may include a control system designated generally as 200 in FIG. 2. Control system 200 may be integrated in any of the handle assemblies described above or some of the components may be provided in a stand-alone unit. Control system 200 includes a processor 202, an input device 204, a display 206, a memory 208, an indicator 210, a motor 212 and a sensor array 214.

Processor 202 may be an integrated circuit or may include analog and/or logic circuitry that may be used to: execute instructions according to inputs provided by the input device 204 or sensor array 214, execute instructions according to a program provided in memory 208; and/or control motor 212 to thereby control the tool assembly 504 to perform any number of functions, including and not limited to clamping tissue therebetween.

Input device 204 may include a keyboard, a touch-screen input device, switches and/or buttons to control operation of the powered surgical instrument 10. Input device 204 may be used to: select between tissue management modes; control tool assembly 504; apply a staple or clamp; and input tissue properties such as tissue type and/or disease.

Display 206 may include a liquid crystal display, a light-emitting diode (LED) display or the like. Display 206 may output a status of the powered surgical instrument, measured tissue properties, number of staples/clips applied, etc.

Control system 200 may also include an indicator 210 that may include at least one light emitting diode (LED) to indicate whether a tissue gap range, between anvil assembly 506 and cartridge assembly 508 of tool assembly 504, has been met.

Sensor array 214 determines tissue properties by detecting the current draw on motor 212 or a dwell effect at tool assembly 504. The detected tissue properties are used to determine the tissue management mode, tissue gap range, firing parameters, motor speed, modulation/pulse of the signal applied to the motor, deployment or non-deployment of staple/clips, etc. The detected tissue properties are used as an input to an iterative adjustment of the clamping pressure and a duration for a tissue management mode.

Memory 208 may be a volatile type memory (e.g., random access memory (RAM)) and/or non-volatile type memory (e.g., flash media, disk media, etc.) that stores programs or sets of instructions for the operation of the powered surgical instrument 10. Such programs include a number of tissue management modes that perform a controlled tissue compression (CTC) operation that may be used to clamp tissue in order to apply a staple or clip to the tissue grasped by tool assembly 504. Memory 208 may also store correlation tables to correlate tissue type and disease type to the requisite tissue gap range and firing parameters that need to the achieved to successfully apply a staple or clip to tissue.

Control system 200 may also include an interface 216 that may be removably coupled to a simulation reload 300 or test platform 400, that will be described hereinbelow. Processor 202 may transmit and/or receive data to simulation reload 300 or test platform 400 through interface 216. In addition, memory 208 may transmit and/or receive data to simulation reload 300 or test platform 400 via interface 216.

During a controlled tissue compression (CTC) operation, motor 212 controls tool assembly 504 to apply a compressive force to tissue grasped between anvil assembly 506 and cartridge assembly 508 of tool assembly 504. Control of motor 212 is based on a CTC program stored in memory 208. Depending on the type of tissue and/or disease type, processor 202 executes the CTC program stored in memory 208. Processor 202 calculates the requisite tissue gap and the firing parameters based on programming code coefficients stored in memory 208 and transmits a signal to motor 212 based on the calculated requisite tissue gap and firing parameters. Motor 212 then controls tool assembly 504 to provide the appropriate tissue compression to achieve an optimal staple formation.

Memory 208 may have a simulation program stored therein to adjust the programming code coefficients used to calculate the firing parameters of instrument 10. Once powered surgical instrument 10 is assembled, powered surgical instrument 10 may be placed in a reload simulation state by processor 202. Powered surgical instrument 10 is fired through a nominal thickness and sensor array 214 measures the current draw on the motor 212. The measured current draw is transmitted to processor 202 which then compares the measured current draw for the simulation state to a predetermined current draw value stored in memory 208 that corresponds to the nominal thickness. Based on the difference between the measured current draw for the simulation state and the predetermined current draw stored in memory 208, processor 202 adjusts the programming code coefficients for the particular powered surgical instrument 10.

Figure 3:
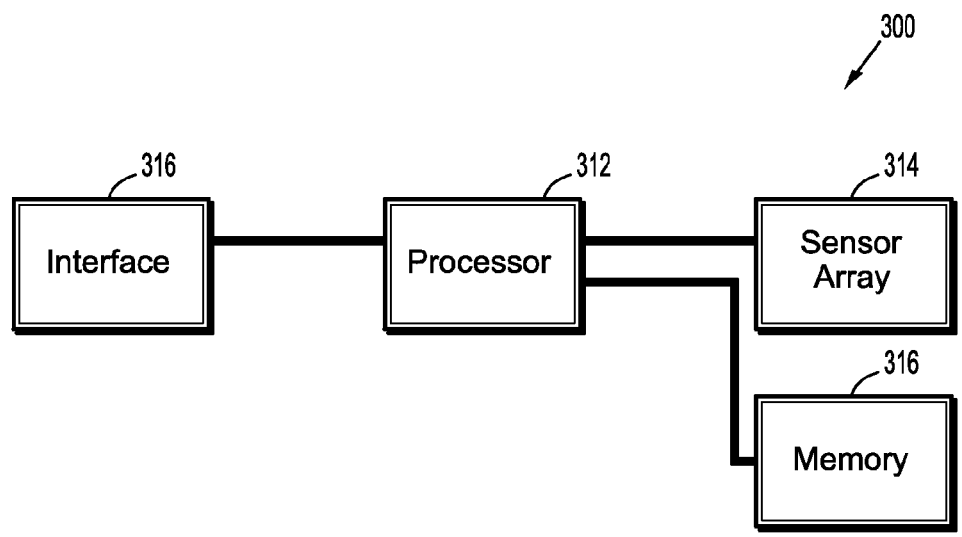
FIG. 3 is a system block diagram of a simulation reload according to an embodiment of the present disclosure.

FIG. 3 depicts a simulation reload 300 in accordance with an embodiment of the present disclosure. After a powered surgical instrument 10 is assembled, instrument 10 is tested using a simulation reload 300 in place of an actual reload 500. Simulation reload 300 is similar to reload 500 and may further include a processor 312, a sensor array 314, and a memory 316. Processor 312 may be an integrated circuit or may include analog and/or logic circuitry that may be used to execute instructions according to inputs provided by sensor array 314 and/or execute instructions according to a program provided in memory 316. Sensor array 314 determines tissue properties by detecting the current draw on motor 212 or a dwell effect at tool assembly 504. Memory 208 may be a volatile type memory (e.g., random access memory (RAM)) and/or non-volatile type memory (e.g., flash media, disk media, etc.) that stores readings from sensor array 314.

Simulation reload 300 may also include an interface 316 that may be removably coupled to interface 216 of control system 200 or irremovably coupled to a test platform 400. Interface 316 may transmit sensor readings from sensor array 314 and/or memory 316 to processor 202 of control system 200.

Simulation reload 300 is loaded into powered surgical instrument 10 to test instrument 10 through a predetermined nominal thickness firing. Sensor array 314 measures the current draw on motor 212 when the powered surgical instrument 10 is used to grasp tissue and simulate a staple firing and stores the measured current draw in memory 216 and/or 316. The measured current draw may be transmitted to processor 202 to adjust the firing parameters for the tested powered surgical instrument 10.

In another embodiment, simulation reload 300 may transmit measurements from sensor array 314 directly to processor 202 via interface 316, or sensor array 214 in control system 200 may be used to measure the current draw on the motor.

Figure 4:
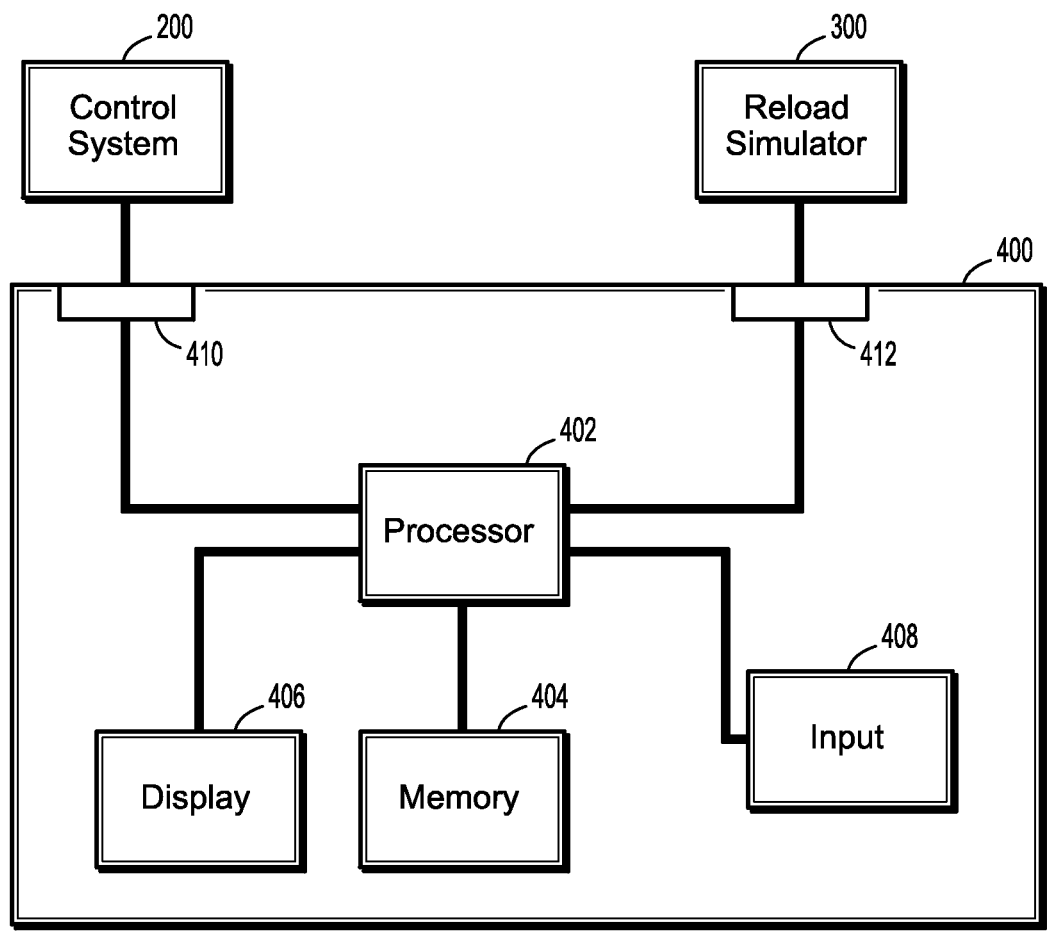
FIG. 4 is a system block diagram of a programming device according to an embodiment of the present disclosure.

FIG. 4 depicts a system block diagram for a test platform 400 according to another embodiment of the present disclosure. As shown in FIG. 4, test platform 400 includes a processor 402, a memory 404, a display 406, an input device 408, an interface 410, and an interface 412.

Processor 402 may be an integrated circuit or may include analog and/or logic circuitry that may be used to: execute instructions according to inputs provided by the input device 408 and/or execute instructions according to a program provided in memory 404. Input device 408 may include a keyboard, a touch-screen input device, switches and/or buttons to control operation of test platform 400. Display 406 may include a liquid crystal display, a light emitting diode display or the like. Memory 404 may be a volatile type memory (e.g., random access memory (RAM)) and/or non-volatile type memory (e.g., flash media, disk media, etc.) that stores programs or sets of instructions for the operation of test platform 400.

After simulation reload 300 is used to test powered surgical instrument 10, simulation reload 300 and powered surgical instrument 10 are removably coupled to first and second interfaces 410 and 412, respectively. The measured current draw stored in simulation reload 300 is downloaded to test platform 400 and stored in memory 404. Using display 406, an operator can see the results of the test firing performed on powered surgical instrument 10 and, using input device 408, reprogram powered surgical instrument 10 to compensate for the individual characteristics of powered surgical instrument 10, e.g., motor variation, friction, manufacturing tolerances, etc.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed:

1. A simulation system comprising:
    a powered surgical instrument including:
        a first processor configured to control operation of the powered surgical instrument;
        a first memory configured to store a tissue compression program; and
        a motor configured to control a reload to apply a compressive force to the tissue by the reload;
    a simulation reload including:
        a second memory configured to store a simulation program; and
        a second processor configured to execute the simulation program,
        wherein the second processor executes the simulation program to measure a current draw on the motor through a nominal thickness firing and wherein the measured current draw is stored in the second memory; and
    a test platform including:
        a first interface configured to be operatively connected to the powered surgical instrument; and
        a second interface configured to be operatively connected to the simulation reload;
        wherein the test platform is configured to adjust the tissue compression program stored in the first memory based on the measured current draw stored in the second memory.

2. The powered surgical instrument of claim 1, wherein the tissue compression program includes programming code coefficients, and wherein the test platform adjusts the programming code coefficients based on the measured current draw.

3. The powered surgical instrument of claim 2, wherein the test platform compares the measured current draw to a predetermined current draw associated with the nominal thickness firing.

4. The powered surgical instrument of claim 3, wherein the difference between the measured current draw and the predetermined current draw is used to adjust the programming code coefficients.

* * * * *